United States Patent
Bailey et al.

(10) Patent No.: US 6,673,381 B2
(45) Date of Patent: *Jan. 6, 2004

(54) USES FOR FOOD AND VITAMIN PREPARATIONS CONTAINING THE NATURAL ISOMER OF REDUCED FOLATES

(75) Inventors: Steven W. Bailey, Mobile, AL (US); June E. Ayling, Mobile, AL (US)

(73) Assignee: South Alabama Medical Science Foundation, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/196,118

(22) Filed: Jul. 16, 2002

(65) Prior Publication Data

US 2002/0176912 A1 Nov. 28, 2002

Related U.S. Application Data

(63) Continuation of application No. 09/888,798, filed on Jun. 25, 2001, now Pat. No. 6,451,360, which is a continuation of application No. 09/418,649, filed on Oct. 15, 1999, now Pat. No. 6,254,904, which is a continuation of application No. 09/117,586, filed as application No. PCT/US97/01870 on Jan. 31, 1997, now Pat. No. 5,997,915.

(60) Provisional application No. 60/010,898, filed on Jan. 31, 1996.

(51) Int. Cl.[7] .............................................. A23L 1/302
(52) U.S. Cl. ......................... 426/72; 426/549; 426/801
(58) Field of Search ........................... 426/72, 549, 801

(56) References Cited

U.S. PATENT DOCUMENTS

| | | |
|---|---|---|
| 1,431,525 A | 10/1922 | Hoffman |
| 2,052,219 A | 8/1936 | Dickens |
| 3,833,739 A | 9/1974 | Pedersen et al. |
| 4,451,571 A | 5/1984 | Allen |
| 4,753,926 A | 6/1988 | Lucas et al. |
| 4,834,987 A | 5/1989 | Lembke et al. |
| 4,940,658 A | 7/1990 | Allen et al. |
| 5,006,655 A | 4/1991 | Miller et al. |
| 5,118,505 A | 6/1992 | Koltringer |
| 5,563,126 A | 10/1996 | Allen et al. |
| 5,624,686 A | 4/1997 | Shimoda et al. |
| 5,795,873 A | 8/1998 | Allen |
| 5,997,915 A | 12/1999 | Bailey et al. |
| 6,011,040 A | 1/2000 | Muller et al. |
| 6,207,651 B1 | 3/2001 | Allen et al. |
| 6,254,904 B1 | 7/2001 | Bailey et al. |
| 6,451,360 B2 | 9/2002 | Bailey et al. |

FOREIGN PATENT DOCUMENTS

| | | |
|---|---|---|
| EP | 0 382 019 A1 | 8/1990 |
| EP | 0 388 827 A1 | 9/1990 |
| EP | 0 482 493 A2 | 4/1992 |
| EP | 0 595 005 A1 | 5/1994 |
| EP | 0 646 322 A1 | 4/1995 |
| JP | 407147911 A | 6/1995 |
| JP | 407291864 A | 11/1995 |
| JP | 408070788 A | 3/1996 |
| WO | WO 97/27764 | 8/1997 |
| WO | WO 01/84962 A2 | 11/2001 |

OTHER PUBLICATIONS

Tamura, T. and Stokstad, E.L.R., Br J Haemo 25:513–532 (1973).
Colman, N. et al., Am J Clin Nutr 28:459–464 (1975).
Perry, J. and Chanarin, I., Br J Haemo 18:329–339 (1970).
Brown, J.P. et al., Gastroenterology 64(2):223–232 (1973).
O'Broin, J.D. et al., Am J Clin Nutr 28:438–444 (1975).
Poncz et al., Journal of Pediatrics, 98:76–69 (1981).
Gregory, J.F. et al., Am J Clin Nutr 55:1147–1153 (1992).
IMS World database accession No. 94:61435 Druglaunch (1994).
Shils et al., eds., Modern Nutrition in Health and Disease, 8th ed., Philadelphia, Pennsylvania: Lea & Febiger, pp. 402–425 (1994).
Shils et al., eds., Modern Nutrition in Health and Disease, 8th ed., Philadelphia, Pennsylvania: Lea & Febiger, pp. 1533–1534 (1994).
Poncz et al., The Journal of Pediatrics, 120:948 (1996).

*Primary Examiner*—Helen Pratt
(74) *Attorney, Agent, or Firm*—Rogalskyj & Weyand, LLP

(57) ABSTRACT

A composition for human or animal consumption for supplying folate which includes a natural isomer of reduced folate, such as (6S)-tetrahydrofolic acid. 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives is disclosed. Such compositions include multivitamin preparations (with or without minerals and other nutrients); breakfast foods such as prepared cereals, toaster pastries and breakfast bars; infant formulas; dietary supplements and complete diet and weight-loss formulas and bars; animal feed (for example pet foods) and animal feed supplements (such as for poultry feed). The amount of the natural isomer of a reduced folate in a composition for human consumption can range between about 5% and about 200% of the daily requirement for folic acid per serving or dose.

39 Claims, No Drawings

USES FOR FOOD AND VITAMIN PREPARATIONS CONTAINING THE NATURAL ISOMER OF REDUCED FOLATES

This application is a continuation of U.S. patent application Ser. No. 09/888,798, filed Jun. 25, 2001, now U.S. Pat. No. 6,451,360, which is a continuation of U.S. patent application Ser. No. 09/418,649, filed Oct. 15, 1999, now U.S. Pat. No. 6,254,904, which is a continuation of U.S. patent application Ser. No. 09/117,586, filed Jul. 31, 1998, now U.S. Pat. No. 5,997,915, which is a 371 of PCT/US97/01870, filed Jan. 31, 1997, which claims the benefit of U.S. Provisional Patent Application Serial No. 60/010,898, filed Jan. 31, 1996.

FIELD OF THE INVENTION

The present invention relates generally to the field of nutrition, and more specifically to food and vitamin preparations containing the natural isomer of reduced folates.

BACKGROUND OF THE INVENTION

The folates are ubiquitous to nearly all forms of life. Humans and many other animals lack the capacity to make their own folate which thus is an essential vitamin, one type of essential nurient. Anemia especially during pregnancy and in the geriatric population was an early indication of a dietary requirement for folate. A major function of folate is to remove one-carbon units from molecules being metabolized and then deliver them to molecules being synthesized. As an example, folate participates in the formation of the nucleic acids. Further, the activity of DNA is controlled, in part, by methylation, and the primary methylating agent of the body (S-adenosylmethionine) is made in a metabolic cycle involving a folate. Many studies have, therefore, focused on the relationship of folate status to cancer susceptibility, especially colorectal adenoma.

The importance of folate to proper growth is clearly evident in the occurrence of neural tube defects in newborn infants. Reports from several countries have shown that a majority of such cases are associated with low folate levels in the mother. The incidence of these defects as well as of cleft lip/palate is considerably reduced when women are given folic acid (I) starting early in pregnancy. Recently, a significant correlation has been discovered between vitamin deficiency, especially of folate, and peripheral vascular disease, a major cause of death. A high percentage of individuals with this affliction have abnormal blood levels of homocysteine, a precursor to methionine in the folate dependent step of the S-adenosylmethonine cycle. Folate deficiency has also been linked to defective maturation of a number of different cell types, to nervous system disorders, and to decreased immune response.

The clear relation of folate intake to health has caused many governmental agencies around the world (such as the U.S. National Reasearch Council) to specify a recommended dietary allowance ("RDA") for folate. In the U.S. these values are used by the Food and Drug Administration to establish the Reference Daily Intake ("RDI") that is listed on food labels, currently 0.4 mg for adults. The highest daily amount of folic acid recommended by a country is 2.0 mg for healthy adults. Many products are available that contain RDI or near RDI levels of folic acid (I) including most daily multiple vitamins. These can be purchased in solid (e.g. tablet, capsule, or powder) or in liquid formulations, both over-the-counter and by prescription. In the U.S. folic acid (I) is also available by itself typically at a dosage of 0.4 mg, but also up to 0.8 mg in health food stores. Many complete diets, infant diets, dietary supplements and weight loss products also contain folic acid (I). In some countries folic acid is added to specific food types as determined by health officials to provide adequate folate to the general population without risking excess consumption. Many breakfast foods, such as cereals, cereal bars, breakfast drink mixes, breakfast bars and toaster pastries have folic acid (I) added at a modest fraction of the RDI, typically 10–50% of the adult value per serving. In many of these uses the folic acid (I) is accompanied by other vitamins, sometimes at RDI dosages, but also at lower or much higher levels. Frequently, though not always, essential mineral nutrients are also present. Further, many products also include compounds hypothesized to have health related value, but which either have not been officially recognized as effective, or for which optimal amounts have not been set. Products such as those described above are meant to fill an important and wide spread need for folate, especially among those whose dietary habits would otherwise preclude intake of a sufficient amount of this vitamin.

Folic acid (I) is a component of many animal and pet foods. It is also included in powders or liquids used as animal feed supplements, often in combination with other nutrients. For example, the National Research Council (NRC) recommends diets containing 0.2 mg and 1.0 mg of folic acid (I) per kg of dry diet (assuming 5 kcal metabolizable energy per gram) for dogs and cats, respectively. For chicks the NRC has recommended 0.55 mg folic acid per kg of diet, although recent literature suggests that the optimal value is about three times higher than this.

The form of folate currently added to all commercial vitamin preparations or which is added to foods. folic acid (I) (also known as pteroyl-L-glutamic acid), is not one of the major forms found in natural fresh foods. The structure of folic acid (I) differs from the most abundant natural folate in several aspects. First, the side-chain of natural folates in almost all fresh foods contains more than one L-glutamic acid moiety. Frequently, five to seven (but covering a considerable span of more or fewer) of this amino acid are linked together into a polyglutamate chain. It is well known, however, that the primary form by which folates are absorbed has only a single glutamate residue. Cleavage of the extra glutamates of dietary folates is usually accomplished by an enzyme in the digestive tract. In this aspect folic acid (I) is not at a disadvantage in comparison to naturally occurring folates.

The second difference between folic acid (I) and natural folates is that whereas the pteridine ring of the former (I) is fully oxidized, natural folates in fresh uncooked foods are mostly present as the tetrahydro forms. Almost all of the known physio-logical functions of folate are performed by tetrahydrofolic acid, (6S)-FH$_4$ (II), or by a one carbon derivative of it illustrated as follows: 5-methyl-(6S)-FH$_4$ (III), 5-formyl-(6S)-FH$_4$ (V), 10-formyl-(6R)-FH$_4$ (V), 5,10-methylene-(6R)-FH$_4$ (VI), 5,10-methenyl-(6R)-FH$_4$ (VII), and 5-formimino-(6S)-FH$_4$ (VIII). The structural formula for each of these compounds is provided below.

I

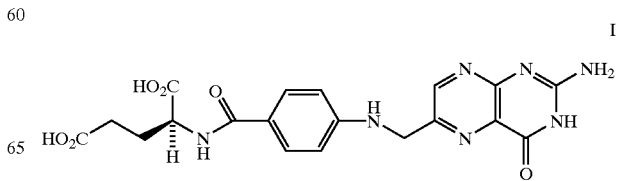

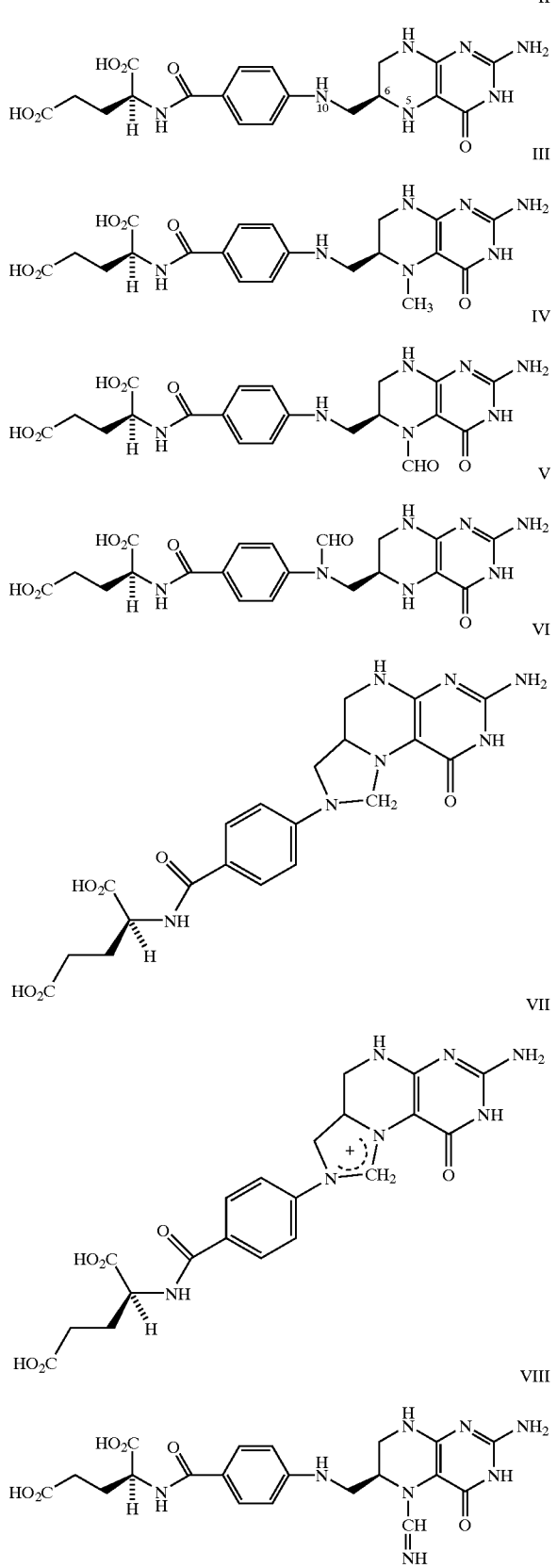

There is no known direct cofactor function for folic acid (I) itself in humans. Some (6S)-tetrahydrofolic acid poly- glutamate is found in plants or animals, but the majority of folate is polyglutamate forms of either 5-methyl-, 5-formyl-(6S)-tetrahydrofolic acid) and in some cases 10-formyl-tetrahydrofolic acid. Presumably, most of the folic acid (I) found in biological food sources results from oxidation, especially on storage. When folic acid (I) is absorbed by the digestive tract it is eventually reduced to active (6S)-tetrahydrofolic acid (II) by the enzyme dihydrofolate reductase.

The oral bioavailability of folic acid (I) has been shown to be widely variable. The literature contains reports of individuals having poor intestinal uptake of folic acid (I) who respond normally to intramuscular injection of folic acid (I), or had normal serum folate status prior to any folic acid challenge. Several small scale investigations in which the values have been averaged have concluded that the oral uptake of several of the reduced folates is similar to folic acid (I). However, there is reason to believe that a segment of the population possesses adequate oral response to reduced folates, but not to oral folic acid (I).

5-Formyl-tetrahydrofolic acid (also known as leucovorin or folinic acid) has long been used in therapeutic doses for several diseases. Examples include rescue from the toxicity of methotrexate chemotherapy, and the synergistic combination with fluorouracil for treatment of various cancers. It is also given to treat acute anemia not due to $B_{12}$ deficiency. 5-Methyl-tetrahydrofolic acid in high doses (for example, 50 mg/day) has been patented for treatment of depression (and other neurological disorders) (EP382019 and EP388827 to Le Grazie 1990, and EP482493 to Le Greca 1992).

That reduced folates have been overlooked as an improved source for providing the RDA level is in part due to the stereochemistry of these compounds. In addition to the single chiral center of the L-glutamate chain in folic acid (I), the tetrahydrofolates contain a second stereochemical center at carbon-6. Chemical reduction of folic acid (I) produces a nearly racemic mixture of the two isomers at this position. This is in contrast to the reduced folates found in nature which all consist of a single diastereoisomer, all having the same L-configuration at carbon-6. (Compounds II–VIII are shown as the natural isomer). For many years only the racemic 6(R,S) mixture of 5-formyl-tetrahydrofolic acid (leucovorin) has been used for therapy of diseases. Recently, however, concern over the possible effects of the unnatural isomer component has resulted in the commercial introduction of the pure natural isomer for these high dose disease treatments by Lederle, although at very high cost. Most therapeutic regimes utilizing leucovorin last a few weeks or perhaps months. The effect of a long term exposure to the unnatural isomer of reduced folates is unknown. For example, although little 5-formyl-(6R)-tetrahydrofolic acid is absorbed, there is considerable uptake of the unnatural isomer of 5-methyl-tetrahydrofolic acid by the intestinal tract and other cells of the body which with continuous intake may lead to adverse consequences.

Until recently, processes for making the natural isomer of reduced folates have been limited in scale, or costly, or both. These include chromatographic separation, enzymatic reduction, and fractional crystallization. The use of reduced folates as a daily source of vitamin requires a method that is applicable to large scale production of the natural isomer having high purity at a cost that will not place a burden on the average consumer.

SUMMARY OF THE INVENTION

The present invention relates to a composition which includes one or more natural isomers of reduced folate and a nutritional substance. The one or more natural isomers of reduced folate is selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof. The nutritional substance is a food preparation, an essential nutrient preparation, or a combination thereof. When the nutritional substance is a food preparation, the food preparation includes two or more food components. Each gram of the food preparation has a natural molar amount, N, of the one or more natural isomers of reduced folate, N being greater than or equal to zero, and each gram of the composition has a total molar amount, T, of the one or more natural isomers of reduced folate greater than N. When the nutritional substance is an essential nutrient preparation, the essential nutrient preparation includes a vitamin other than ascorbic acid.

The present invention also relates to method for increasing the folate content of a nutritional substance. The method includes providing a nutritional substance selected from the group consisting of a food preparation, an essential nutrient preparation, and combinations thereof. The method further includes incorporating into the nutritional substance a molar amount of one or more natural isomers of reduced folate selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof. When the nutritional substance is a food preparation, the food preparation comprises two or more food components. When the nutritional substance is an essential nutrient preparation, the essential nutrient preparation comprises a vitamin other than ascorbic acid.

A significant number of people are folate deficient; especially vulnerable are those whose life style does not include sufficient fresh food sources of folates. An object of this invention is nutritional compositions in which the natural isomer of tetrahydrofolic acid, or a derivative thereof, is substituted for the usual folic acid (I) for the satisfaction or partial satisfaction of the dietary requirement for this vitamin. While some may not be greatly affected by the inclusion of reduced folates in multivitamin preparations and breakfast foods, still a substantial number of people, and thus the average health of the population, will be improved by addressing the needs of those for whom folic acid (I) bioavailability is poor. Consumer confidence with regard to consumption of a food or other nutritional product will be increased with the knowledge that the folate content is chemically identical to the most abundant natural forms of this vitamin, except for the advantageous absence of multiple glutamate residues. A further advantage is that health agencies will be aided in recommending optimal levels when a more uniformly absorbed form of folate is widely used.

DETAILED DESCRIPTION OF THE INVENTION

The present invention relates to a composition which includes one or more natural isomers of reduced folate and a nutritional substance. Natural isomers of reduced folate suitable for use in the present invention include, for example, (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid. Other natural isomers of reduced folate suitable for use in the present invention include the polyglutamyl, such as the diglutamyl, triglutamyl, tetraglutamyl, pentaglutamyl, and hexaglutamyl, derivatives of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid. Any or all of the natural isomers of reduced folate can be present in its chirally pure form, or, alternatively, the composition can optionally contain a molar amount of one or more unnatural isomers of reduced folate, such as (6R)-tetrahydrofolic acid, 5-methyl-(6R)-tetrahydrofolic acid, 5-formyl-(6S)-tetrahydrofolic acid, 10-formyl-(6S)-tetrahydrofolic acid, 5,10-methylene-(6S)-tetrahydrofolic acid, 5,10-methenyl-(6S)-tetrahydrofolic acid, 5-formimino-(6R)-tetrahydrofolic acid, and polyglutamyl derivatives thereof. The molar amount of the natural isomer of reduced folate can be equal to the molar amount of its corresponding unnatural isomer (as where the unnatural and natural isomer are present as a racemic mixture), or, preferably, the natural isomer of reduced folate can be present in a molar amount greater than the molar amount of the corresponding unnatural isomer. The total molar amount of the one or more natural isomers of reduced folate present in the composition can be between 5% and 200% of a human daily requirement for folate per a customarily consumed quantity of the composition. As used herein, the total molar amount of the one or more natural isomers of reduced folate includes natural isomers of reduced folates which are naturally present in the nutritional substance as well as natural isomers of reduced folates which might have been added to the nutritional substance. The customarily consumed quantity of various compositions depends, of course, on the nature of the composition. Where the composition includes a food preparation, the customarily consumed quantity is the amount of the food preparation customarily consumed per eating occasion, for example, as set forth by the U.S. Food and Drug Administration for the purpose of establishing realistic and consistent serving sizes for use in food labeling. Examples of customarily consumed quantities for various food groups can be found in 21 C.F.R. §101.12, which is hereby incorporated by reference.

The human daily requirement for folate varies from person to person, depending on factors such as body weight, age, health, sex, and the like. Suitable values for the human daily requirement for folate include RDI and RDA values, promulgated, respectively, by the FDA and the National Research Council ("NRC"). Presently, RDI values, expressed in terms of micrograms of folic acid (nanomoles of folic acid), are 400 µg (907 nmoles) for adults and 800 µg (1814 nmoles) for pregnant women. In view of this, the compositions of the present invention can have between 45 and 1814 nmoles or between 91 and 3625 nmoles of folate per customarily consumed quantity of the nutritional substance. Current RDA values are published in *National Research Council: Recommended Daily Allowances*, 10th ed., Washington, D.C. (1989), which is hereby incorporated by reference. They are, again expressed in terms of micrograms of folic acid (nanomoles of folic acid), 25 µg (57 nmoles) for infants 0–6 months of age, 35 µg (79 nmoles) for infants 6 months to one year of age, 50 µg (113 nmoles) for infants 1–3 years of age, 100 µg (227 nmoles) for infants 7–10 years of age, 200 µg (454 nmoles) for male adults, 180

μg (408 nmoles) for female adults other than pregnant adult females, and 400 μg (907 nmoles) for pregnant females. In view of this, typical compositions of the present invention can have between 2.8 and 113 nmoles, between 4 and 159 nmoles, between 28 and 227 nmoles, between 11 and 454 nmoles, between 22 and 907 nmoles, between 20 and 816 nmoles, or between 45 and 1812 nmoles of folate per customarily consumed quantity of the nutritional substance. Suitable values for the human daily requirement for folates are also established by the World Health Organization as 7.03 nmoles/kg of body weight. For pregnant women the value calculated based upon body weight should be increased by about 454 to about 680 nmoles.

The total molar amount of the one or more natural isomers of reduced folate present in the composition can, alternatively, be between 5% and 3000% of an animal daily requirement for folate per a customarily consumed quantity of the nutritional substance. The animal, whose daily requirement for folate is referred to above, can be, for example, a dog, a cat, a chicken, a cattle, a domestic animal, a goat, a horse, a mink, a fox, a sheep, or a swine. Suitable values for the an animal's daily requirement for folate are promulgated, for example, by the NRC in *Nutrient Requirements of Domestic Animals* (Washington: National Academy Press), particularly in those publications having the following subtitles: "Nutrient Requirements of Beef Cattle," Seventh Revised Edition (1996, ISBN 0-309-05426-5); "Nutrient Requirements of Cats," Revised Edition (1986, ISBN 0-309-03682-8); "Nutrient Requirements of Dairy Cattle," Sixth Revised Edition, Update (1989, ISBN 0-309-03826-X); "Nutrient Requirements of Dogs, Revised (1985, ISBN 0-309-03496-5); "Nutrient Requirements of Fish," (ISBN 0-309-04891-5); "Nutrient Requirements of Goats: Angora, Dairy, and Meat Goats in Temperate and Tropical Countries," (ISBN 0-309-03185-0); "Nutrient Requirements of Horses," Fifth Revised Edition, (1989, ISBN 0-309-03989-4); "Nutrient Requirements of Laboratory Animals," Fourth Revised Edition (1995, ISBN 0-309-05126-6); "Nutrient Requirements of Mink and Foxes," Second Revised Edition, (1982, ISBN 0-309-03325-X); "Nutrient Requirements of Poultry," Ninth Revised Edition, (1994, ISBN 0-309-04892-3); "Nutrient Requirements of Sheep," Sixth Revised Edition, (1985, ISBN 0-309-03596-1); and "Nutrient Requirements of Swine," Ninth Revised Edition, (1988, ISBN 0-309-03779-4) (collectively referred to as "NRC Animal Nutrient Requirements"), which are hereby incorporated by reference.

As indicated above the nutritional substance can be a food preparation or an essential nutrient preparation. Essential nutrient preparations are materials which contain one or more essential nutrients. Where only one essential nutrient is present in the essential nutrient preparation, that essential nutrient can be a vitamin other than ascorbic acid. The essential nutrient preparation can, alternatively, include a vitamin other than ascorbic acid and, in addition, ascorbic acid. As used herein, essential nutrients are those nutrients which are required to sustain health but which cannot be effectively produced by one or more animals or by humans. Examples of essential nutrients are compiled in a number of published sources, including *Modern Nutrition in Health and Disease,* 8th ed., Shils et al., eds., Philadelphia: Lea and Febiger (1994), which is hereby incorporated by reference. Essential nutients are meant to include essential vitamins and provitamins thereof, essential fats, essential minerals, such as those minerals for which daily values have been recommended, and essential amino acids. One example of an essential nutrient preparation is a formulation which contains a vitamin and a caloric content of less than 2.5 cap per dry gram, preferably less than 2 cal per dry gram, most preferably less than 1.8 cap per dry gram. Essential nutrient preparations also include those materials which contain at least one vitamin in an amount greater than 15%, preferably greater than 20%, more preferably greater than 40% of the U.S. adult RDA for that essential nutrient per gram of essential nutrient preparation. Still other suitable essential nutrient preparations contain at least two vitamins, each in an amount greater than 10%, preferably greater than 15%, more preferably greater than 20% of the U.S. adult RDA for that essential nutrient per gram of essential nutrient preparation. Suitable essential nutrient preparations are commonly referred to as dietary supplements, vitamin supplements, and mineral supplements, multiple vitamin supplements, and the like, and are typically available commercially in the form of pills, tablets, capsules, powders, syrups, and suspensions. Preferably, the essential nutrient composition contains at least one essential nutrient in an amount greater than 25%, more preferably greater than 50%, and most preferably greater than or equal to 100% of the daily requirement for that essential nutrient per customarily consumed quantity of the essential nutrient preparation.

As indicated above, the nutritional substance can also be a food preparation. Food preparations are materials which contain one or more amino acid, carbohydrate, or fat, which are suitable for human or animal consumption, and which are not essential nutrient preparations. It is preferred that the food preparation be a two or more component food preparation. For example, a two or more component food preparation can be a mixture of two or more one-component foods. One component foods are foods which are derived substantially from a single natural source. A small percentage of the one-component food can be derived from a second natural source, but that percentage, by weight, is preferably less than 5%, more preferably less than than 1%, more preferably less than 0.1%. One component foods include, for example, sugar, unsweetened juice, nectar, or puree from a single species of plant, such as unsweetened apple juice (including a blend of different varieties of apple juice), grapefruit juice, orange juice, apple sauce, apricot nectar, tomato juice, tomato sauce, tomato puree, and the like. Grain plants of a single species and materials produced from grain plants of a single species, such as corn syrup, rye flour, wheat flour, oat bran, and the like are also considered to be one component foods. Alternatively, the two or more component food preparation can be a mixture of one or more one component foods and one or more essential nutrients. Preferably, the amount of at least one of the one or more essential nutrients present in the two component food is greater than the amount of the at least one essential nutrient that is naturally present collectively in the one or more one component foods. For example, where the essential nutrients are vitamin X and vitamin Y and where the one component food is orange juice and where the orange juice naturally contains vitamin X and vitamin Y in amounts "Nx" and "Ny", respectively, it is preferred that the composition contain vitamin X and vitamin Y in amounts "Tx" and "Ty", respectively, so that Tx is greater than Nx, Ty is greater than Ny, or both.

Food preparations particularly well suited to the practice of the present invention include breakfast foods, such as prepared cereals, toaster pastries, and breakfast drink mixes; infant formulas; dietary supplements; complete diet formulas; and weight-loss preparations, such as weight-loss drinks and weight-loss bars.

The food preparation can be one which naturally contains no natural isomer of reduced folate. Alternatively, it can contain a natural molar amount of a natural isomer of reduced folate. For purposes of this application, the molar amount of natural isomer of reduced folate (i.e., collectively, the number of moles of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof) contained per gram of food is designated "N". For some foods, the molar amount of natural isomer of reduced folate naturally present is known. For others, the molar amount of natural isomer of reduced folate can be determined by a number of sensitive and specific methods, such as microbial growth dependence, folate binding protein based assays, high-performance liquid chromatography ("HPLC") and gas chromatography ("GC"). Suitable methods are described, for example, in Cossins, E. A., "Folates in Biological Materials," in *Folates and Pterins*, Vol. 1, Blakley et al., eds., New York: John Wiley & Sons, pp. 1–60 (1984), which is hereby incorporated by reference.

The molar amount of natural isomer of reduced folate present in the composition of the present invention is greater that the molar amount of natural isomer of reduced folate present in the food preparation. For purposes of this application, the molar amount of natural isomer of reduced folate (i.e., collectively, the number of moles of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof) contained per gram of composition is designated "T". Thus, T necessarily must be greater than N. Preferably, T/N is greater than 105%; more preferably, it is greater that 110%; and, most preferably, it is greater than 120%.

As indicated above, the composition can, optionally, include one or more unnatural isomers of reduced folate. When present in the composition, the one or more unnatural isomers of reduced folate is preferably present in a molar amount which is less than T minus N.

The present invention also relates to a method for increasing the folate content of a nutritional substance. The nutritional substance can be a food preparation, an essential nutrient preparation, or a combination of a food preparation and an essential nutrient preparation. The folate content of the nutritional substance is increased by incorporating one or more natural isomers of reduced folate into or with the nutritional substance. This can be achieved by methods well known in the art of food and essential nutrient preparation, such as by homogenizing, coating, spraying, coarsely mixing, tossing, kneading, pilling, and extruding one or more unnatural isomer of reduced folate, singly or in combination, onto or with the nutritional substance.

One or more of the one or more natural isomers of reduced folate that are added to the nutritional substance in accordance with the present invention can be substantially chirally pure or each of the one or more natural isomers of reduced folate can be chirally pure. Alternatively, one or more of the one or more natural isomers of reduced folate can be present in a mixture with one or more unnatural isomers of reduced folate. The molar amount of the one or more natural isomers of reduced folate and the one or more unnatural isomers of reduced folate present in the mixture added to the nutritional substance can be the same, as in the case where a racemic mixture is added, or they can be different. Preferably the molar amount of the natural isomer exceeds the molar amount of the unnatural isomer. Additionally or alternatively, unnatural isomer of reduced folate can be incorporated in a separate step subsequent to or prior to incorporating the one or more natural isomers of reduced folate into the nutritional substance. It is preferred that the collective molar amount of unnatural isomer of reduced folate added before, during, and/or after the addition of natural isomer of reduced folate be less than the collective molar amount of natural isomer added.

Natural isomers of reduced folates that are substantially chirally pure can be prepared by any suitable method, including, for example, by the method described in U.S. Pat. No. 5,350,851 to Bailey et al., which is hereby incorporated by reference.

When the nutritional substance is a food preparation, in addition to incorporating a natural isomer of reduced folate, one or more essential nutrients, optionally, can be incorporated into the food preparation. The essential nutrients can, for example, be added to the food preparation before, during, or after addition of the natural isomer of reduced folate.

The compositions of the present invention can be used to increase a subject's dietary intake of folate by administering the composition to the subject. The subject can be an animal, such as a dog or a cat; alternatively, the subject can be a human. Certain classes of individuals are viewed to be especially benefitted by increasing dietary intake of folate. These include pregnant females; females who have had a miscarriage; females who have carried a fetus having a neural tube defect, a cleft lip defect, or a cleft palate defect; and humans who suffer vascular disease.

The compositions can also be used to treat a subject afflicted with intestinal malabsorption, especially folate malabsorption. When treating a subject afflicted with intestinal malabsorption, the amount of composition administered is preferably effective to cause an increase in the subject's blood folate level. More preferably, the amount administered is effective to produce blood folate levels in an normal range, as determined by conventional blood-folate analysis methods, such as with the Quanta Phase II assay from BioRad Laboratories, Hercules, Calif.

The compositions can be administered enterally, such as orally, intragastricly, or transpyloricly. Many factors that may modify the action of the composition can be taken into account by those skilled in the art; e.g. body weight, sex, diet, time of administration, route of administration, rate of excretion, condition of the subject, and reaction sensitivities and severities. Administration can be carried out continuously or periodically, such as once daily, or once with every meal.

Compositions containing the natural isomer of reduced folates are preferably for enteral consumption (enteral including oral, intragastric, or transpyloric), and are of any, food preparation, food supplement, essential nutrient preparation, or vitamin preparation. Typical examples of such food or vitamin preparations are those to which folic acid (I) is currently added for use by either humans or other animals. Natural isomer means a tetrahydrofolate having the natural configuration at both the glutamate α-and the pteridine 6-carbons. More specifically, these compositions are, but are not limited to, multivitamin (with or without minerals and other nutrients) preparations (such preparations can be in solid, liquid or suspension forms); breakfast foods such as prepared cereals, breakfast drink mixes, toaster pastries and breakfast bars; infant formulas; dietary supplements and complete diet and weight-loss formulas and bars;

animal feed or animal feed supplements (for example, for poultry), and pet foods. The natural isomer of reduced folates can also be used in products which health officials might in the future deem an appropriate vehicles for satisfaction of the daily folate requirement. The composition of the present invention can include a natural isomer of a tetrahydrofolate, such as II–VIII, preferably the monoglutamate form, in a vitamin formulation preferably containing at least one other vitamin (for example another vitamin such as a B vitamin) other than ascorbic acid (vitamin C), although ascorbic acid can be an additional component. Such nutrients or vitamins can be those intended for either human or animal use. Other ingredients may also be present, such as fillers, binding agents, stabilizers, sweeteners, including nutitive sweeteners (e.g. sucrose, sorbitol and other polyols) and non-nutritive sweeteners (e.g. saccharin, aspartame, and acesulfame K), colorants, flavors, buffers, salts, coatings, and the like that are known to those skilled in the art of vitamin formulation.

For many applications of the described reduced folates (II through VIII) 5-methyl-(6S)-tetrahydrofolic acid (III), 5-formyl-(6S)-tetrahydrofolic acid (IV), and 5,10-methenyl-(6R)-tetrahydrofolic acid (VII) are preferred. All of the reduced folates are to differing extent subject to oxidation by air. Several factors influence this susceptibility, foremost being derivatization of the 5-nitrogen which considerably slows oxidation. The 5-methyl- and 5-formyl derivatives are the most abundant forms of folate found in most tissues of the body. The predominate folate in human blood is 5-methyl-(6S)-tetrahydrofolic acid (III).

In using tetrahydrofolates for increasing the folate in a nutritional composition, several factors should be considered. Many nutrients are unstable to processing, including several of the vitamins. For example, vitamins A, $B_1$ (thiamin), and ascorbic acid are especially labile under some conditions. Many procedures are known for enhancing the stability of the various nutrients such as pH and moisture control of the composition. Components which are to a degree incompatible with each other, for example ascorbic acid with the more oxidized forms of iron or copper, can be made to be present heterogeneously in the composition. Nutrients which are unstable to heat are often added after baking steps; for example, vitamins are often sprayed onto breakfast cereals subsequent to toasting. Nutrients which are unstable to air can be packaged in a reduced oxygen condition, and/or in containers that have low or no permeability to oxygen. These and other procedures known to those skilled in the art are useful for maintaining folates in their natural reduced form.

The rate of oxidation of a reduced folate in the presence of air is increased in water solutions. The shelf life of liquid preparations will be greatly extended if they are preferably kept in air-tight containers. Replacing air with an inert gas such as nitrogen or argon also retards loss. Reduced folates can also be protected from oxidation by a number of reducing agents and antioxidants, the most relevant of these being other vitamins that are often included in multivitamin mixtures or nutritional compositions. Ascorbic acid has been used for protection of reduced folates in biochemical experiments and procedures for the laboratory analysis of biological samples. Such protection need not be limited to use of ascorbic acid or other vitamins; other agents suitable for human or animal consumption are useful, for example iso-ascorbic acid and certain thiols, such as glutathione. Further, known packaging and formulation technologies which increase the stability of compounds such as ascorbic acid or other air labile materials (for example, coated forms, blister packaging, and use of reduced metals or metal complexes) are useful for the maintenance of reduced folates. The salt form of a reduced folate also somewhat affects stability and solubility, and this can be optimized for the needs of each product. The pH of the final composition can also be optimized according to the stability properties of the particular reduced folate derivative used and of the other components present, as is well understood in the arts of processing nutrients and of folate compounds. For example, in the presence of moisture 5,10-methenyl-(6R)-$FH_4$ (VII) can be transformed into 10-formyl-(6R)-$FH_4$ and 5-formyl-(6S)-$FH_4$ (IV) (the latter also a preferred compound) in a pH dependent manner. Compositions containing 5,10-methenyl-(6R)-$FH_4$ (VII) are most stable to oxidation when either substantially dry and/or have an acidity less than about pH 4. With proper attention to the above factors, the lability of reduced folates need not limit the life of a product, especially with III and IV which are more resistant than ascorbic acid to many oxidation reactions.

The substitution of a reduced folate for folic acid (I) should take into account the differences in molecular weights of the various forms. For example, the current U.S. Reference Daily Intake of 0.4 mg of folic acid (I) corresponds to 0.91 micromole using an anhydrous molecular weight of 441.4. The effective molecular weight of reduced folates depends upon the derivative employed (i.e. II–VIII), the salt form, and water content. For example, 0.91 micromole of 5-formyl-(6S)-tetrahydrofolic acid (IV) calcium salt-pentahydrate would weigh 0.545 mg, and 0.91 micromole of 5-methyl-(6S)-tetrahydrofolic acid (III) disodium salt would weigh 0.456 mg. Several salt forms of the reduced folates are described in the literature, such as hydrochloride, sodium, potassium, magnesium, calcium, and others and having various water content. For each of these forms a similar calculation can be made. The amount required to achieve the mole equivalent to a desired fraction of the RDI would then be that fraction of this new weight. As an example, 25% RDI of 5-methyl-(6S)-tetrahydrofolic acid (III) disodium salt would be 0.25×0.456=0.114 mg, the mole equivalent of 0.10 mg of folic acid (I). Previous investigations of groups of individuals having a normal uptake of folic acid (I) have shown that the bioavailability of the reduced folates is similar on a mole basis.

As mentioned above, loss of nutrients during processing, especially of foods is well known to those skilled in this art. An often practiced procedure is the addition of an initial excess, an "overage", of a particular nutrient or nutrients, such that the final post-processing amount is at the desired level. Many highly sensitive and specific methods are known (such as microbial growth dependence, folate binding protein based assays, HPLC and GC) for the analysis of folates, in both the reduced and oxidized forms as well as for their various derivatives. These assays permit adjustment of the added amount of the natural isomer of a reduced folate so as to yield the desired final amount subsequent to processing and packaging. The range of the natural isomer of a reduced folate in the composition of this invention is preferably that fulfilling between about 5% and about 200% of the RDI of humans for folate, and should be taken to encompass both the situation where allowance is made for processing loss, and also where no such allowance is made. Separate RDA dosages are specified for different groups of people, for example pregnant and non-pregnant women. Further, the RDI level although relying on RDA values, can be different from RDA values. The above range of "between about 5% and about 200% of the RDI for folate" should be taken to operate independently on each of these separate RDA and RDI specifications, or their foreign equivalents, as presently stated or as modified in the future. For the purpose of this invention these several specifications shall be referred to as the daily requirement for folate. Unless the recommended dietary allowance for folate in humans is increased, the maximum final amount of the natural isomer of a reduced folate in composition for human use in satisfying the daily requirement for folate preferably should not exceed about 4.5 micromole per dose or customarily consumed serving. However, for individuals afflicted with intestinal malabsorption, such as celiac disease or tropical sprue, compositions containing higher amounts of the natural isomer of a reduced folate will be useful.

For the purpose of this invention an essential nutrient composition can be a dietary supplement or the like, the substantial folate component of which is derived from substantially pure tetrahydrofolic acid or derivative thereof, such as compounds II through VIII. Essential nutrient compositions encompassed by this invention comprise the natural isomer of a reduced folate preferably within the above described range along with other vitamins and/or other nutrients which are preferably each present in an amount that is considered to be safe. In formulating compositions for animal consumption manufacturers often considerably exceed the dosage recommended by the NRC for folate (by 10-fold, 20-fold, or more in some cases), not only to overcome losses during processing, but also to cover occasions of possible increased need for folate, such as during antibiotic treatment. Other vitamin and nutrient components can be present in amounts that vary considerably from NRC recommendations. The following examples are given to further illustrate the invention, and are not intended to limit its scope in any way.

EXAMPLES

1) A typical ready to eat breakfast cereal: corn (and/or other grains), sugar, salt, malt flavoring, such that a 30 g serving provides about 2 g of protein, 26 g total carbohydrate, and 330 mg of sodium, also containing per serving size vitamin A palmitate (15% of RDI), ascorbic acid (25% of RDI), reduced iron (45% of RDI), vitamin D (10% of RDI), thiamin hydrochloride (25% of RDI), riboflavin (25% of RDI), niacinamide (25% of RDI), pyridoxine hydrochloride (25% of RDI), and 0.114 mg of 5-methyl-6(S)-tetrahydrofolic acid (III) disodium salt (the mole equivalent of 0.1 mg folic acid, 25% of RDI).

2) A typical daily multivitamin tablet: calcium carbonate, ascorbic acid (60 mg, 100% RDI), gelatin, vitamin E acetate (30 I.U., 100% RDI), starch, niacinamide (20 mg, 100% RDI), hydroxypropyl-methylcellulose, calcium pantothenate (10 mg, 100% RDI), calcium silicate, hydroxypropylcellulose, pyridoxine hydrochloride (2 mg, 100% RDI), riboflavin (1.7 mg, 100% RDI), thiamin mononitrate (1.5 mg, 100% RDI), beta carotene & vitamin A acetate (5000 I.U., 100% RDI), sodium hexametaphosphate, magnesium stearate, vitamin D (400 I.U., 100% RDI), vitamin $B_{12}$ (6 $\mu$g, 100% RDI), lecithin, and 0.437 mg of 5-methyl-6(S)-tetrahydrofolic acid (III) magnesium salt (the mole equivalent of 0.4 mg folic acid, 100% of RDI).

3) A typical daily multivitamin and minerals tablet: calcium phosphate (130 mg of elemental calcium), magnesium hydroxide & stearate (100 mg, 25% RDI), cellulose, potassium chloride, ascorbic acid (60 mg, 100% RDI), gelatin, ferrous fumarate (18 mg elemental iron, 100% RDI), zinc sulfate (15 mg, 100% RDI), modified cellulose gum, vitamin E acetate (30 I.U., 100% RDI), citric acid, niacinamide (20 mg, 100% RDI), magnesium stearate, hydroxypropyl-methylcellulose, calcium pantothenate (10 mg, 100% RDI), selenium yeast, polyvinylpyrrolidone, hydroxypropylcellulose, manganese sulfate, silica, copper oxide (2 mg, 100% RDI), chromium yeast, molybdenum yeast, pyridoxine hydrochloride (2 mg, 100% RDI), riboflavin (1.7 mg, 100% RDI), thiamin mononitrate (1.5 mg, 100% RDI), beta carotene & vitamin A acetate (5000 I.U., 100% RDI), potassium iodide (150 $\mu$g, 100% RDI), sodium hexametaphosphate, biotin (30 $\mu$g, 10% RDI), vitamin D (400 I.U., 100% RDI), vitamin $B_{12}$ (6 $\mu$g, 100% RDI), lecithin, and 0.545 mg 5-formyl-(6S)-tetrahydrofolic acid (IV) calcium salt-pentahydrate (the mole equivalent of 0.4 mg of folic acid, 100% RDI).

4) A typical daily multivitamin and minerals tablet for older adults: calcium carbonate, calcium phosphate (200 mg Ca, 20% RDI; 48 mg phosphorous, 5% RDI), magnesium oxide, magnesium stearate (100 mg, 25% RDI), potassium chloride (80 mg, 2% RDI), microrystalline cellulose, ascorbic acid (60 mg, 100% RDI), gelatin, d' l-alfa-tocopheryl acetate (45 I.U., 150% RDI), modified food starch, maltodextrin, crospovidone, reduced iron (4 mg, 22 RDI), hydroxypropyl methylcellulose, niacinamide (20 mg, 100% RDI), zinc oxide (15 mg, 100% RDI), calcium pantothenate, manganese sulfate (3.5 mg), vitamin D (400 I.U., 100% RDI), titanium dioxide, vitamin A and β-carotene (5000 I.U., 100% RDI), stearic acid, pyridoxine hyrochloride (3 mg, 150% RDI), riboflavin (1.7 mg, 100% RDI), silicon dioxide, copper oxide (2 mg, 100% RDI), dextrose, thiamin mononitrate (1.5 mg, 100% RDI), triethyl citrate, polysorbate 80, chhromium chloride (130 $\mu$g), artificial colors, potassium iodide ((150 $\mu$g, 100% RDI), sodium metasilicate (2 mg), sodium molybdate (160 $\mu$g), borates, sodium selenate (20 $\mu$g), biotin (30 $\mu$g, 10% RDI), sodium metavanadate (10 $\mu$g), cyanocobalamin (25 $\mu$g, 417% RDI), nickelous sulfate (5 $\mu$g), and phytonadione, and 5,10-methenyl-(6R)-tetrahydrofolic acid hydrochloride (VII) (0.44 mg, the mole equivalent of 0.4 mg of folic acid, 100% RDI).

5) A typical complete diet drink: water, sugar, calcium and sodium caseinates, maltodextrin, high-oleic safflower oil, soy protein, soy oil, canola oil, cocoa, sodium and potassium citrates, calcium carbonate and phosphate (250 mg Ca, 25% RDI), magnesium chloride and phosphate (100 mg Mg, 25% RDI), sodium chloride, soy lecithin, choline chloride, flavor, ascorbic acid (30 mg, 50% RDI), carrageenan, zinc sulfate (5.6 mg, 37% RDI), ferrous sulfate (4.5 mg Fe, 25% RDI), alfa-tocopheryl acetate (11.3 I.U., 37.7% RDI), niacinamide (5 mg, 25% RDI), calcium pantothenate (2.5 mg, 25% RDI), manganese sulfate (1.3 mg), copper salt (25% RDI), vitamin A palmitate (1250 I.U., 25% RDI), thiamin hydrochloride (0.375 mg, 25% RDI), pyridoxine hydrochloride (0.5 mg, 25% RDI), riboflavin (0.425 mg, 25% RDI), biotin (75 $\mu$g, 25% RDI), sodium molybdate (38 $\mu$g), chromium chloride (25 $\mu$g), potassium iodide (37.5 $\mu$g, 25% RDI), sodium selenate (18 $\mu$g), phylloquinone (vitamin K,), cyanocobalamin (1.5 $\mu$g, 25% RDI), vitamin $D_3$ (100 I.U., 25% RDI), and 0.136 mg 5-formyl-(6S)-tetrahydrofolic acid (IV) calcium salt-pentahydrate (the mole equivalent of 0.1 mg of folic acid, 25% RDI), packaged in an air-tight container, and supplying about 225 calories.

6) A typical enhanced B-vitamin/tetrahydrofolate tablet: dibasic calcium phosphate, pyridoxine hydrochloride (50 mg, 2,500% RDI), cellulose, stearic acid, magnesium stearate, and 0.912 mg of 5-methyl-6(S)-tetrahydrofolic acid (III) disodium salt (the mole equivalent of 0.8 mg folic acid, 200% of RDI for adults, 100% RDA for pregnant women).

7) A typical poultry feed vitamin supplement: (amounts per kg of diet) vitamin A (trans retinyl acetate, 5500 I.U.), vitamin E (11 I.U.), menadione sodium bisulfite (1.1 mg), vitamin $D_3$ (1100 I.U.), riboflavin (4.4 mg), vitamin $B_{12}$ (10 µg), vitamin $B_6$ (3.0 mg), thiamin mononitrate (2.2 mg), biotin (0.3 mg), ethoxyquin (125 mg), and 2.0 mg 5-formyl-(6S)-tetrahydrofolic acid (IV) calcium salt-pentahydrate (the mole equivalent of 1.45 mg of folic acid).

8) A typical dry cat food: ground yellow corn, corn gluten meal, soybean meal, poultry by-product meal, animal fat, fish meal, meat and bone meal, ground wheat, phosphoric acid calcium carbonate, dried animal digest, salt, brewers dried yeast, potassium chloride, dried whey solubles, choline chloride, dried skimmed milk, taurine, L-lysine, zinc oxide, ferrous sulfate, niacin, vitamin A, vitamin $D_3$, vitamin $B_{12}$, calcium pantothenate, citric acid, manganese sulfate, riboflavin supplement, biotin, copper salt, thiamine mononitrate, pyridoxine hydrochloride, menadione sodium bisulfate complex, such that the crude protein is not less than 31%, crude fat is not less than 8%, crude fiber is not more than 4.5%, moisture is not more than 12%, calcium is not less than 1.2%, phosphorous is not less than 1.0%, sodium chloride is not more than 1.5%, the metabolizable energy is about 3,600 kcal/kg, taurine, iron, vitamins A, $D_3$, $B_{12}$, and E are at least 100% of levels recommended by the Association of American Feed Control Officials, and containing not less than 0.97 mg/kg diet 5-methyl-6(S)-tetrahydrofolic acid (III) calcium salt dihydrate (the mole equivalent of 0.8 mg/kg diet of folic acid).

9) A typical soy based infant formula: 75.5% water; 13% sucrose; 6.6% oleo oil: coconut, high oleic (safflower or sunflower), and soybean oils; 3.8% soy protein isolate; (protein 2.7 g, fat 5.3 g, carbohydrate 10.2, linoleic acid 500 mg); potassium citrate and bicarbonate (potassium 105 mg); monobasic potassium and dibasic calcium phosphates (phosphorous 63 mg); soy lecithin; taurine; calcium carrageenan; calcium hydroxide, chloride and citrate (calcium 90 mg); sodium chloride (sodium 30 mg); L-methionine; zinc (Zn 0.8 mg), ferrous (Fe 1.8 mg), and manganese (Mn 30 µg) sulfates; copper salt (Cu 70 µg); taurine; L-carnitine; potassium iodide (I 9 µg); ascorbic acid (8.3 mg); choline chloride; alpha-tocopheryl acetate (1.4 I.U.); niacinamide (750 µg); vitamin A palmitate and beta-carotene (300 I.U.); calcium pantothenate (450 µg); thiamin hydrochloride (100 µg); riboflavin (150 µg); pyridoxine hydrochloride (62.5 µg); vitamin $K_1$ (15 µg); biotin (5.5 µg); vitamin $D_3$ (60 I.U.); cyanocobalamin (0.3 µg); and 9.1 µg of 5-methyl-6(S)-tetrahydrofolic acid (III) calcium salt dihydrate (the mole equivalent of 7.5 µg of folic acid), packaged in an air-tight container (amounts are per 150 ml of 1:1 diluted formula).

One skilled in the art will readily appreciate that the present invention is well adapted to carry out the objects and obtain the ends and advantages mentioned. While the above description contains many specificities, these should not be construed as limitations on the scope of the invention, but rather as an exemplification of preferred embodiments thereof. Changes therein and other uses will occur to those skilled in the art which are encompassed within the spirit of the invention as defined by the scope of the claims and their legal equivalents.

What is claimed:

1. A method for reducing a female's risk of having a miscarriage and/or of having a fetus with a neural tube defect, a cleft lip defect, and/or a cleft palate defect, said method comprising administering, to the female, prior to and/or during pregnancy, a composition which comprises:

one or more natural isomers of reduced folate selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof; and a nutritional substance selected from the group consisting of a food preparation, an essential nutrient preparation, and combinations thereof;

wherein, when the nutritional substance is a food preparation, the food preparation comprises two or more food components and each gram of said food preparation has a natural molar amount, N, of said one or more natural isomers of reduced folate, wherein N is greater or equal to zero and wherein each gram of said composition has a total molar amount, T, of said one or more natural isomers of reduced folate greater than N;

wherein, when the nutritional substance is an essential nutrient preparation, the essential nutrient preparation comprises a vitamin other than ascorbic acid.

2. A method according to claim 1, wherein, when the nutritional substance is an essential nutrient preparation and when the composition comprises an amount of 5-formyl-(6S)-tetrahydrofolic acid, the composition further comprises 5-formyl-(6R)-tetrahydrofolic acid, or, if present, the composition further comprises 5-formyl-(6R)-tetrahydrofolic acid in an amount less than the amount of 5-formyl-(6S)-tetrahydrofolic acid present in the composition.

3. A method according to claim 1, wherein the essential nutrient preparation further comprises ascorbic acid.

4. A method according to claim 1, wherein the one or more natural isomers of reduced folate is (6S)-tetrahydrofolic acid or a polyglutamyl derivative thereof.

5. A method according to claim 1, wherein the one or more natural isomers of reduced folate is 5-methyl-(6S)-tetrahydrofolic acid or a polyglutamyl derivative thereof.

6. A method according to claim 1, wherein the one or more natural isomers of reduced folate is 5-formyl-(6S)-tetrahydrofolic acid or a polyglutamyl derivative thereof.

7. A method according to claim 1, wherein the one or more natural isomers of reduced folate is 10-formyl-(6R)-tetrahydrofolic acid or a polyglutamyl derivative thereof.

8. A method according to claim 1, wherein the one or more natural isomers of reduced folate is 5,10-methylene-(6R)-tetrahydrofolic acid or a polyglutamyl derivative thereof.

9. A method according to claim 1, wherein the one or more natural isomers of reduced folate is 5,10-methenyl-(6R)-tetrahydrofolic acid or a polyglutamyl derivative thereof.

10. A method according to claim 1, wherein the one or more natural isomers of reduced folate is 5-formimino-(6S)-tetrahydrofolic acid or a polyglutamyl derivative thereof.

11. A method according to claim 1, wherein each of the one or more natural isomers of reduced folate is substantially chirally pure.

12. A method according to claim 1, wherein said method is carried out to reduce the female's risk of having a miscarriage.

13. A method according to claim 1, wherein said method is carried out to reduce the female's risk of having a fetus with a neural tube defect.

14. A method according to claim 1, wherein said method is carried out to reduce the female's risk of having a fetus with a cleft lip defect and/or a cleft palate defect.

15. A method according to claim 1, wherein the female is a human female.

16. A method according to claim 1, wherein the female is a pregnant female.

17. A method according to claim 1, wherein the female is a non-pregnant female.

18. A method according to claim 1, wherein the female is one who has previously had a miscarriage and/or one who has previously carried a fetus having a neural tube defect, a cleft lip defect, a cleft palate defect, or combinations thereof.

19. A method according to claim 1, wherein said administering is carried out periodically.

20. A method according to claim 1, wherein said administering is carried out daily.

21. A method according to claim 1, wherein the one or more natural isomers of reduced folate is 5-methyl-(6S)-tetrahydrofolic acid or a polyglutamyl derivative thereof; wherein the composition further comprises 5-methyl-(6R)-tetrahydrofolic acid or a polyglutamyl derivative thereof; and wherein the 5-methyl-(6S)-tetrahydrofolic acid or polyglutamyl derivative thereof and the 5-methyl-(6R)-tetrahydrofolic acid or polyglutamyl derivative thereof are present in equal molar amounts.

22. A method for treating and/or preventing vascular disease in a subject, said method comprising administering, to the subject, a composition which comprises:
   one or more natural isomers of reduced folate selected from the group consisting of (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives thereof; and
   a nutritional substance selected from the group consisting of a food preparation, an essential nutrient preparation, and combinations thereof;
   wherein, when the nutritional substance is a food preparation, the food preparation comprises two or more food components and each gram of said food preparation has a natural molar amount, N, of said one or more natural isomers of reduced folate, wherein N is greater or equal to zero and wherein each gram of said composition has a total molar amount, T, of said one or more natural isomers of reduced folate greater than N;
   wherein, when the nutritional substance is an essential nutrient preparation, the essential nutrient preparation comprises a vitamin other than ascorbic acid.

23. A method according to claim 22, wherein, when the nutritional substance is an essential nutrient preparation and when the composition comprises an amount of 5-formyl-(6S)-tetrahydrofolic acid, the composition further comprises no 5-formyl-(6R)-tetrahydrofolic acid, or, if present, the composition further comprises 5-formyl-(6R)-tetrahydrofolic acid in an amount less than the amount of 5-formyl-(6S)-tetrahydrofolic acid present in the composition.

24. A method according to claim 22, wherein the essential nutrient preparation further comprises ascorbic acid.

25. A method according to claim 22, wherein the one or more natural isomers of reduced folate is (6S)-tetrahydrofolic acid or a polyglutamyl derivative thereof.

26. A method according to claim 22, wherein the one or more natural isomers of reduced folate is 5-methyl-(6S)-tetrahydrofolic acid or a polyglutamyl derivative thereof.

27. A method according to claim 22, wherein the one or more natural isomers of reduced folate is 5-formyl-(6S)-tetrahydrofolic acid or a polyglutamyl derivative thereof.

28. A method according to claim 22, wherein the one or more natural isomers of reduced folate is 10-formyl-(6R)-tetrahydrofolic acid or a polyglutamyl derivative thereof.

29. A method according to claim 22, wherein the one or more natural isomers of reduced folate is 5,10-methylene-(6R)-tetrahydrofolic acid or a polyglutamyl derivative thereof.

30. A method according to claim 22, wherein the one or more natural isomers of reduced folate is 5,10-methenyl-(6R)-tetrahydrofolic acid or a polyglutamyl derivative thereof.

31. A method according to claim 22, wherein the one or more natural isomers of reduced folate is 5-formimino-(6S)-tetrahydrofolic acid or a polyglutamyl derivative thereof.

32. A method according to claim 22, wherein each of the one or more natural isomers of reduced folate is substantially chirally pure.

33. A method according to claim 22, wherein the subject is a human subject.

34. A method according to claim 22, wherein the subject is one who suffers from vascular disease.

35. A method according to claim 22, wherein the subject is one who suffers from peripheral vascular disease.

36. A method according to claim 22, wherein said administering is carried out periodically.

37. A method according to claim 22, wherein said administering is carried out daily.

38. A method according to claim 22, wherein the subject has an abnormal blood level of homocysteine.

39. A method according to claim 22, wherein the one or more natural isomers of reduced folate is 5-methyl-(6S)-tetrahydrofolic acid or a polyglutamyl derivative thereof; wherein the composition further comprises 5-methyl-(6R)-tetrahydrofolic acid or a polyglutamy derivative thereof; and wherein the 5-methyl-(6S)-tetrahydrofolic acid or polyglutamyl derivative thereof and the 5-methyl-(6R)-tetrahydrofolic acid or polyglutamyl derivative thereof are present in equal molar amounts.

* * * * *